(12) United States Patent
Epps

(10) Patent No.: US 6,205,589 B1
(45) Date of Patent: Mar. 27, 2001

(54) MEDITATION ENHANCING ARTICLE

(76) Inventor: Napoleon Epps, 144 Onondaga Dr., Forest Height, MD (US) 20745

( * ) Notice: Subject to any disclaimer, the term of this patent is extended or adjusted under 35 U.S.C. 154(b) by 0 days.

(21) Appl. No.: 09/281,275

(22) Filed: Mar. 30, 1999

(51) Int. Cl.[7] ................................................ A42B 1/00
(52) U.S. Cl. ................................................ 2/171; 2/171.2
(58) Field of Search ................. 2/171.2, 422, 200.1, 2/209.13, 209.14, 171

(56) References Cited

U.S. PATENT DOCUMENTS

| | | | |
|---|---|---|---|
| 3,234,563 | * | 2/1966 | Tabbat ................................ 2/196 |
| 3,496,575 | * | 2/1970 | Neckermann et al. ............... 2/171 |
| 4,167,075 | * | 9/1979 | Pugh et al. ........................ 40/617 |
| 4,605,000 | * | 8/1986 | Anguita ........................ 128/201.25 |
| 5,224,495 | * | 7/1993 | Robinson ........................... 2/209 |
| 5,708,983 | * | 1/1998 | Cross et al. ........................ 2/171 |

* cited by examiner

*Primary Examiner*—Bibhu Mohanty
(74) *Attorney, Agent, or Firm*—Alfred F. Hoyte, Jr.

(57) ABSTRACT

A meditation enhancing apparatus is provided. The apparatus is a head covering which is made of a highly conductive metal such as copper. The head covering or helmet has several ports which are adapted to hold crystals, the ports being connected to conduits. The conduits serve to hold the crystals in position directly in front of the user's eyes and temples, as well as to conduct electromagnetic and other energy to the user's brain. The user may select crystals which have been effective in enhancing previous meditation sessions for placement in the device.

4 Claims, 2 Drawing Sheets

MEDITATION ENHANCING ARTICLE

BACKGROUND OF THE INVENTION

1. Field of the Invention

The present invention concerns a meditation apparatus. More specifically, it relates to an improved meditation enhancing apparatus which facilitates and enhances the performance of virtually any meditation method.

2. Description of the Prior Art

Meditation methods and various devices for enhancing meditation are well known in the art. As will be seen, the simplicity and effectiveness of my invention is not rivaled in the prior art.

U.S. Pat. No. 4,167,075 issued to Pugh et al. discloses a meditation aid which has a frame which defines a geometric shape. The device is large enough to accommodate at least one person and may be suspended from the ceiling. The user may then conduct his meditation method inside the aid. By contrast, the present invention comprises a device which has a plurality of panels defining a geometric shape, which is preferably a pyramid. The device is small enough to be portable and may be positioned on a user's head during meditation.

U.S. Pat. No. 5,134,740 issued to Summer discloses a device which promotes proper seating of the user during meditation. The device has a tapered support member upon which the user places his legs. The support allows for sustained periods of meditation without circulation problems in the legs By contrast, the present invention contemplates a portable meditation aid which allow the user to assume any position he desires. The device has a plurality of crystals placed therein and positioned to enhance the user's meditation. The user can then perform his meditation ritual in whatever position he desires.

None of the above inventions and patents, taken either singly or in combination, is seen to describe the instant invention as claimed.

SUMMARY OF THE INVENTION

Briefly, the invention comprises a meditation enhancing apparatus. The apparatus is a head covering which is made of a highly conductive metal such as copper. The head covering or helmet has several ports which are adapted to hold crystals, the ports being connected to conduits. The conduits serve to hold the crystals in position directly in front of the user's eyes and temples, as well as to conduct electromagnetic and other energy to the user's brain. The user may select crystals which have been effective in enhancing previous meditation sessions.

Accordingly, it is a principal object of the invention to provide a new and improved meditation method and device therefor.

It is a major object of this invention to provide an improved meditation method and device therefor which uses both electrical/electromagnetic conductors and crystals.

It is another object of the invention to provide such an improved meditation method and device where the user may choose a particular meditation ritual to use with the method and device of the present invention.

It is another object of the invention to provide such an improved meditation method and device where the crystals may be selectively removed.

It is still another object of the invention to provide an improved meditation method and device where the device is inexpensive and easy to manufacture.

It is another object of the invention to provide an improved meditation device which is lightweight and portable and does not require electrical power.

It is yet another object of the invention to provide an improved illuminated inspection device which has an integrated handle, battery enclosure, and pivoting mechanism.

Finally, it is a general object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Referring now to FIGS. 1–4, the meditation enhancing device of the present invention, generally indicated by the numeral 10, is shown. The device 10 of the present invention is designed to be lightweight, portable, and relatively easy to use. The device 10 is preferably made of a highly conductive metal such as copper, but any electrically conductive material may be used. Alternatively, any rigid material such as wood or plastic may be used to support the crystals in place.

The primary purpose of the device 10 is to hold "meditation enhancing" crystals in place so that the user may benefit from the crystals during meditation. It is generally accepted that certain crystals can be used to enhance meditation or to generate or focus "energy" that can be used to enhance one's sense of emotional or physical well being. While the exact nature of any energy emanating from or phenomena associated with these crystals is not known with scientific certainty, it is assumed that at least some portion of this energy is electromagnetic (EM) in nature. In order to attract EM energy it is known to use an antenna or other primarily metallic or conductive structure to capture EM waves which are then guided or focused to a single point or points. In the device 10 of the present invention, EM energy in the ambient environment is collected by or guided to crystals which are held in position by strategically placed structural members.

Figure 1:
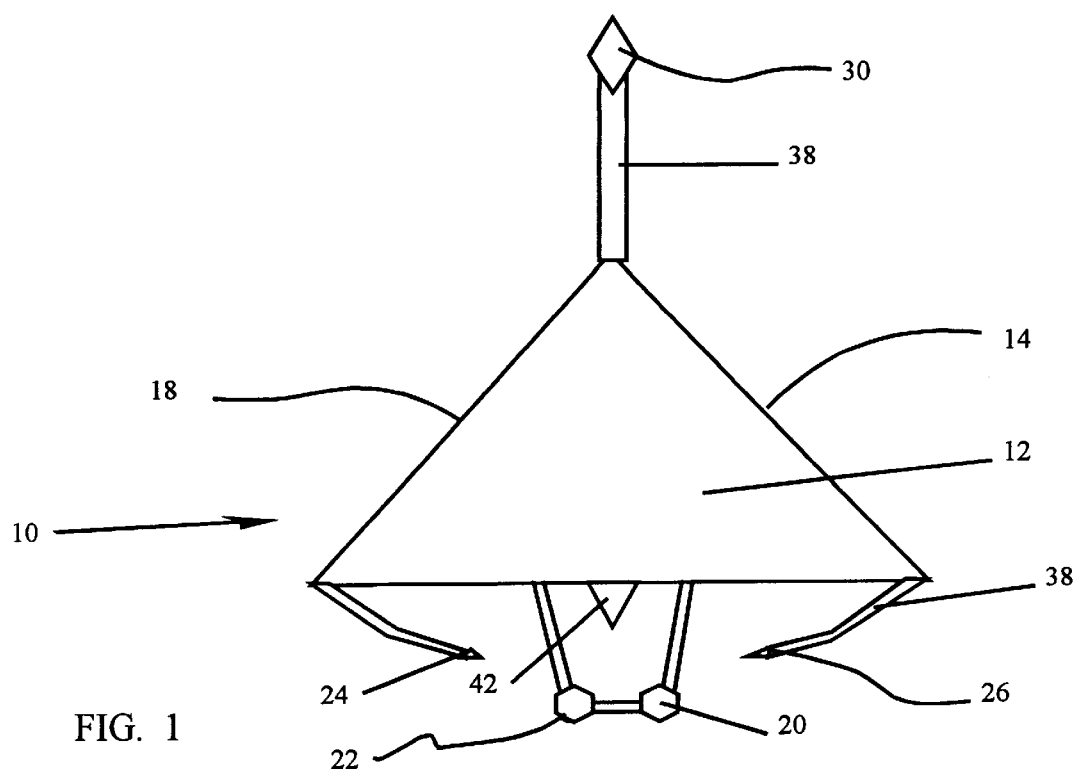
FIG. 1 is a front view of a meditation enhancing device made in accordance with the disclosure of the present invention.
Figure 3:
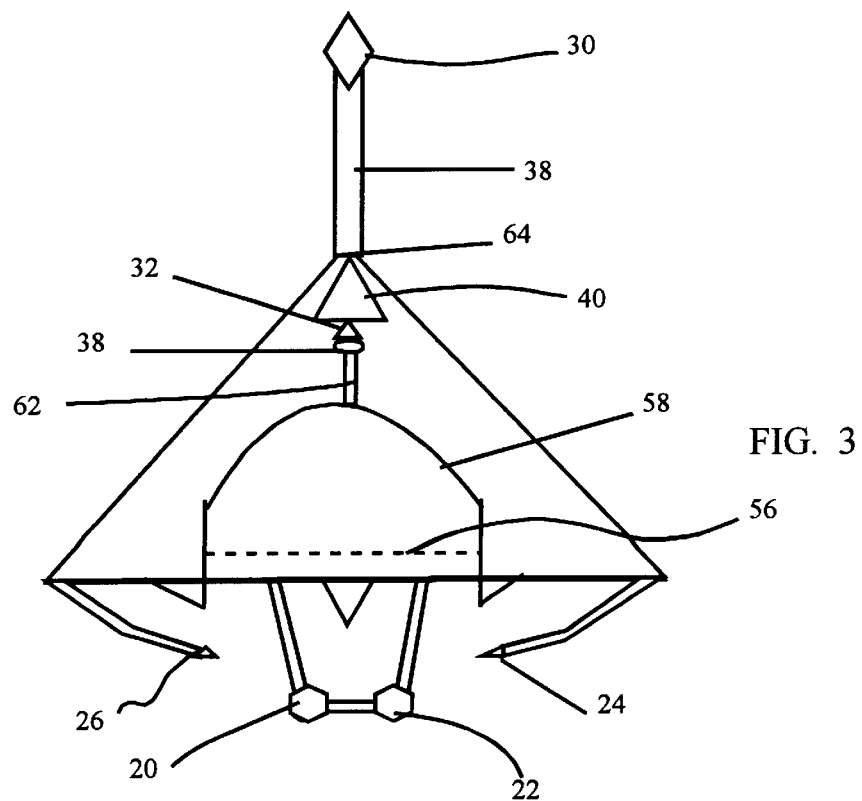
FIG. 3 is a front view, partly in section, of the meditation enhancing device made in accordance with the disclosure of the present invention.
Figure 2:
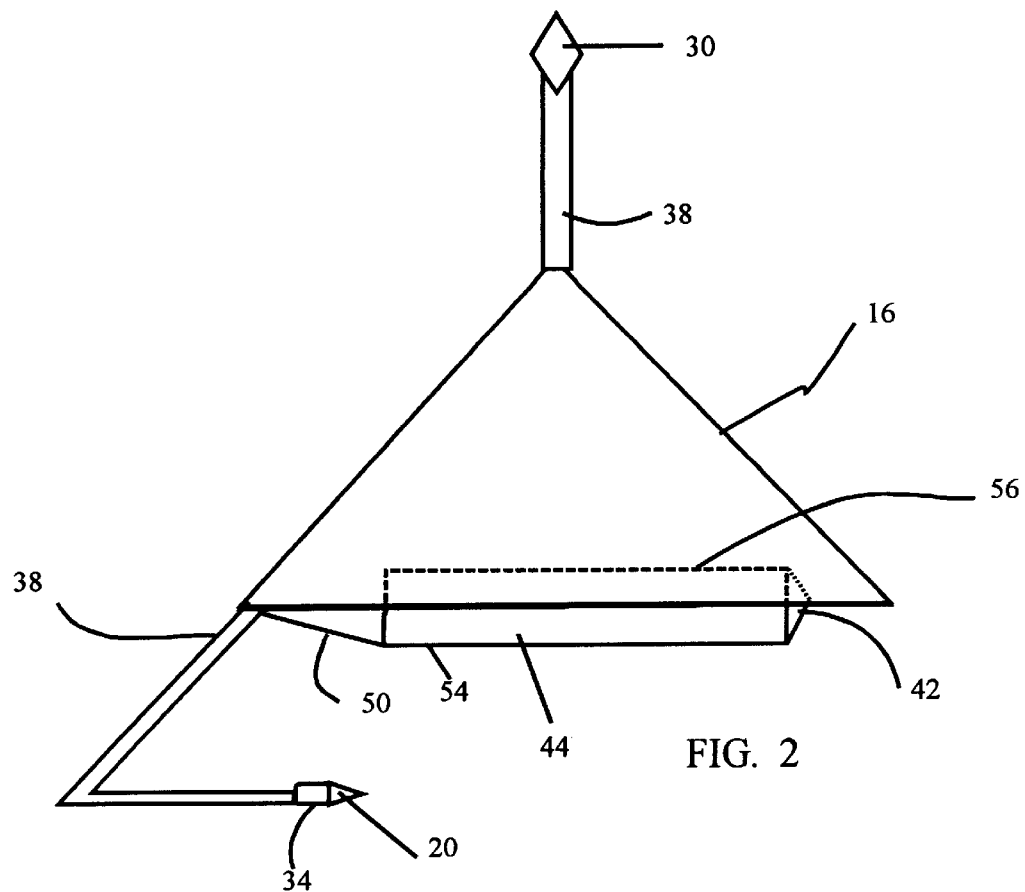
FIG. 2 is a side view of the meditation enhancing device made in accordance with the disclosure of the present invention.
Figure 4:
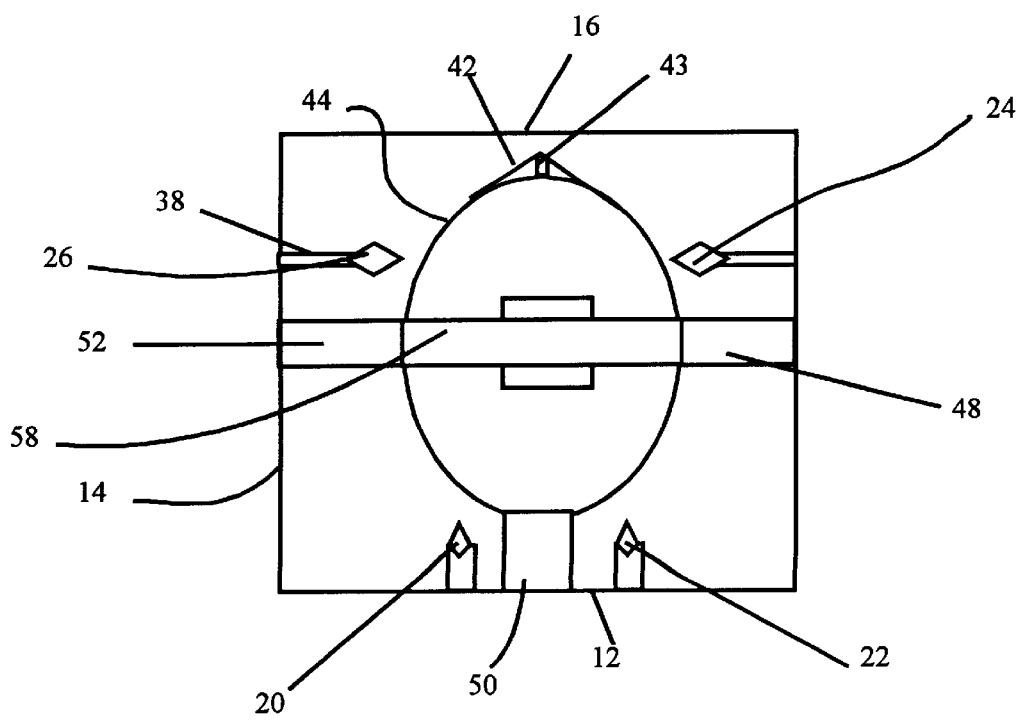
FIG. 4 is a bottom view of the meditation enhancing device made in accordance with the disclosure of the present invention.

The front view of the device, shown in FIG. 1 shows the position of all of the crystals which are mounted on the exterior of the device 10. It can be seen that the overall shape of the device 10 is pyramidal, and has four main body panels 12–18 which may be joined by welding if the panels are made of metal. In the preferred embodiment, the panels 12–18 are made of copper and joined by welding. The panels 12–18 must be made of copper or other material which has a conductivity greater than copper.

The crystals 20–32, which are preferably quartz, are held in position by receptacles 34 which may be adjustable to accommodate crystals of different sizes/diameters. Alternatively, the receptacles 34 may be removable from the device 10 by way of, e.g., of threaded engagement with support members/conduits 38. If the receptacles 34 are removable, replacement receptacles 34 having different diameters may be selectively employed.

The support members 38 serve two purposes. First they are used to conduct EM or other energy to or from the crystals 20–32. Second, they are used to hold the crystals 20–32 in the correct position. The device 10 is constructed to hold at least 6 crystals in position about the user's head. The crystals 20–32 are positioned to stimulate different areas of the brain of the user. The crystals 20, 22 are positioned proximate the frontal lobe. Crystals 24, 26 are positioned proximate the temples and the optic nerve. Crystals 30, 32 are directed to crown of the head of the user. It should also be mentioned that the support members 38 may be made to be adjustable to accommodate users who require a particular positioning of the crystals 20–32.

In addition to the crystals 20–32, a pair of pyramids 40, 42 are mounted inside the device 10. The pyramids 40, 42 are also positioned to stimulate the respective areas of the brain to which they are proximate as will be explained in more detail later. Pyramid 42 also includes a crystal 43, which is embedded therein or attached thereto. It is widely accepted that pyramids may also be used to generate and/or capture EM or other types of energy which may be used to promote a feeling of emotional well being among users. It is assumed, of course, that the user has accepted the general theories associated with both pyramid and crystals and is using the device primarily as a means to position the crystals of his/her choosing in a position about the head most advantageous to enhancing meditation.

In order to support the device on the users head, an annular band 44 sized and shaped for placement on a typical head is supported within the device 10 by braces 48–52 which are attached to sides 18, 12, and 14 respectively on one end, preferably by welding or gluing a substantial surface portion of the brace 48–52 to the respective side to ensure durability. The opposite ends of braces 48–52 are connected to the band 44 at the bottom edge 54 thereof. Connected to the top edge 56 of the band 44, and extending from one side to the other is an arcuate band 58 which serves as a weight bearing member which supports the weight of the device 10 upon the top of the user's head. It can be readily appreciated that the band 58 also serves to position the various crystals 20–32 when the device is upon the user's head and thus may be advantageously fabricated to be adjustable. For instance, a flexible strap assembly (not shown) allowing for adjustment to the effective length of the straps may be employed. The band 44 may have pyramid 42 attached thereto. Alternatively, the pyramid 42 may be made integral with the band 44, e.g., by welding. Band 58 has crystal 32 attached thereto by rod 62 which is securely attached to the band 58. Suspended directly above the crystal 32 is pyramid 40 which is connected to the apex 64 of the device 10 by rod 68.

In operation, the user first places the desired crystals in the receptacles 34. Then, the device 10 is placed on the user's head with the front panel 12 positioned so that crystals 20, 22 are directly in front of the user's eyes, and pyramid 42 is at the back of the user's head. The user may then proceed with whatever meditation ritual she/he desires with the device 10 remaining in place.

It is to be understood that the provided illustrative examples are by no means exhaustive of the many possible uses for my invention.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims:

I claim:

1. A device for enhancing meditation comprising:

a substantially pyramidal main body having four triangular side panels and an open bottom through which a user's head may be positioned;

a plurality of support members attached to said main body, each of said support members including receptacles appended to one end, the receptacles holding at least one crystal;

whereby said crystals may be selectively placed in position about the user's head.

2. The device of claim 1 where said device includes support means attached to inner surfaces of said sides, said support means serving to help position the device about a users head.

3. The device of claim 1 where said device has front, side, and rear panels, said front, side, and rear panels having said support members extending therefrom and serving to position crystals at the front and sides of a user's head.

4. The device of claim 2 where said support means includes an annular band having a pyramid attached thereto, said pyramid attached proximate the rear panel.

* * * * *